United States Patent [19]

des Courieres et al.

[11] Patent Number: 5,273,945
[45] Date of Patent: Dec. 28, 1993

[54] ZEOLITE CATALYST OF HEXAGONAL STRUCTURE AND ITS APPLICATION

[75] Inventors: Thierry des Courieres, Lyon; Jean-Louis Guth, Brunstatt; Jöel Patarin, Mulhouse; Catherine Zivkov, Orthez, all of France

[73] Assignee: Societe Nationale Elf Aquitaine, Courbevoie, France

[21] Appl. No.: 777,299

[22] PCT Filed: Apr. 8, 1991

[86] PCT No.: PCT/FR91/00286
§ 371 Date: Jan. 17, 1992
§ 102(e) Date: Jan. 17, 1992

[87] PCT Pub. No.: WO91/15294
PCT Pub. Date: Oct. 17, 1991

[30] Foreign Application Priority Data

Apr. 9, 1990 [FR] France .................... 90 04501

[51] Int. Cl.$^5$ .................... B01J 29/08
[52] U.S. Cl. .................... 502/61; 502/66; 502/68; 502/79
[58] Field of Search .................... 502/66, 74, 79, 61, 502/68

[56] References Cited

U.S. PATENT DOCUMENTS 5,098,686 3/1992 Delprato et al. .................... 423/703

FOREIGN PATENT DOCUMENTS 140023 11/1981 Japan .................... 502/60
179014 11/1982 Japan .................... 502/60

*Primary Examiner*—Carl F. Dees
*Attorney, Agent, or Firm*—Burgess, Ryan & Wayne

[57] ABSTRACT

A catalyst is provided which contains 1 to 99 wt. % of a zeolite related to faujasite and having a hexagonally symmetrical structure and an Si:Al ratio between 3 and 30. The compensation cations of this zeolite consist partly or wholly of cations of one or more elements chosen from H, B, Al, Ga, In, rare earth metals and transition metals. The catalyst can also contain up to 15%, referred to the total weight of the binder and zeolite, of a catalytically active metal of the noble, non-noble transition or other type which is not already present in the compensation cations of the zeolite. The catalyst can be used in acid catalysis reactions carried out on hydrocarbon feedstock, in particular in fluidized bed catalytic cracking.

12 Claims, No Drawings

ZEOLITE CATALYST OF HEXAGONAL STRUCTURE AND ITS APPLICATION

BACKGROUND OF THE INVENTION

1) Field of the Invention

The invention relates to a catalyst based on a zeolite of hexagonal structure related to faujasite and with a high Si:Al ratio. It also relates to the application of the said catalyst to acidic catalysis reactions carried out on hydrocarbon feedstocks.

2) Background Art

Zeolites have many industrial applications. They are employed in particular in the field of adsorbents, detergents or industrial catalysis. In this last field, most of the applications such as catalytic cracking of distillates under vacuum or of residues to petrol or the hydrocracking of distillates under vacuum to diesel fuel are satisfied by catalysts containing a zeolite of the faujasite type, called zeolite Y and having a synthesis Si:Al ratio of between 1.5 and 3.

Thermal and hydrothermal stability of this zeolite and consequently of the catalysts which contain it remains low and the said zeolite must be subjected to post-synthesis treatments to improve the said stability and more generally the performance of the said catalysts. To obtain an increase in the thermal and hydrothermal stability of the said zeolite it is advisable to increase its network Si:Al ratio and for this purpose it is possible to use various treatments, among which there may be mentioned techniques such as steam treatment optionally followed by washing of the aluminium-containing debris with acid (U.S. application Nos. 3,493,519, and 3,506,400), treatment with ethylenediaminetetraacetic acid (G.T. Kerr, J. Phys. Chem., 72 (1968), p. 2594), treatment with $SiCl_4$ (H.K. Beyer, I.M. Belenykaja, F. Hange, M. Tielen, O.J. Grobet and P.A. Jacobs, J. Chem. Soc., Farad. Trans. 1, 81 (1985), pages 2889 to 2901) or treatment using ammonium fluorosilicate $(NH_4)_2SiF_6$ (U.S. application No. 4,503,023).

All these treatments are troublesome, and this results in an increase in the cost of the final catalyst. Furthermore, such treatments give rise to structural changes in the treated zeolites, resulting in the appearance of faults which can impair the performance of the catalysts including these treated zeolites.

It has been found that zeolites of hexagonal structure related to faujasite and with a synthesis Si:Al ratio higher than 3 can form the basis of excellent catalysts for cracking, hydrocracking, isomerisation or disproportionation reactions, these zeolites exhibiting, inter alia, a high density of acidic sites of intermediate or high strength and an excellent thermal and hydrothermal stability and being also capable of undergoing, with much fewer inconveniences than zeolite Y, owing to their higher lattice Si:Al ratio, the optional post-synthesis treatments intended, if need be, to increase the said ratio.

SUMMARY OF THE INVENTION

The invention therefore proposes a catalyst which is characterised in that it comprises, by weight, y% of an inorganic binder and z% of a zeolite with a structure of hexagonal symmetry related to faujasite, y and z being numbers such that $1 \leq y \leq 99$ and $1 \leq z \leq 99$ with $y+z=100$, the said zeolite having an Si:Al ratio ranging from 3 to 30, preferably from 3 to 20, and parameters a, b and c of its hexagonal lattice such that 1.72 nm $\leq a=b \leq 1.75$ nm and 2.80 nm $\leq c \leq 2.86$ nm and corresponding to a formula which, normalised to a hexagonal lattice, is written $$(uM_1^{1+})(vM^{n+})[(SiO_2)_{96-x}(AlO_2)]^{x-}(tH_2O)$$

with, in this formula, $M^{n+}$ denoting cations of at least one element of valence n chosen from H, B, Al, Ga, In, the rare earth metals and the transition metals, $M_1^{1+}$ denoting cations of at least one metal of valency q chosen from alkali metals and alkaline-earth metals, and u, v, x and t denoting numbers such that $t \geq 0$ depending on the degree of hydration of the zeolite, $t=0$ in the case of a completely anhydrous zeolite, and that $qu+vn \geq x$ with $0.5 \, x \leq vn \leq x$, preferably $0.8 \, x \leq vn \leq x$, and $3 < x \leq 24$.

DESCRIPTION OF THE PREFERRED EMBODIMENTS

In the catalyst according to the invention the weight percentages y of inorganic binder and z of zeolite are preferably such that $4 \leq y \leq 96$ and $4 \leq z \leq 96$ with $y+z=100$.

In addition to the binder and to the zeolite, the catalyst may also contain, based on the weight of the binder and zeolite combined, up to 15% and preferably up to 10% of at least one catalytically active metal present in the elemental state or in the form of a metal compound and chosen from noble metals such as palladium, platinum, rhodium and iridium, nonnoble transition metals such as nickel, cobalt, molybdenum and tungsten, and certain other metals such as gallium.

In the formula of the zeolite, $M_1^{1+}$ denotes in particular cations of at least one element chosen from Na, K, Li, Cs, Ca, Sr and Ba, while $M^{n+}$ denotes especially cations of at least one element chosen from H, Al, B, Ga, In, transition metals such as Ag, Co, Ni and rare earths such as La, Ce, Pr and Nd.

A process for the preparation of the zeolite which can be employed for the production of the catalyst runs through the formation of the alkaline form of the zeolite, that is to say of the form in the case of which the cations of the zeolite are alkali metal cations, and this alkaline form is then converted into the protonated form and the protonated zeolite is optionally subjected to exchange reactions to introduce the desired cations $M^{n+}$ other than the protons $H^+$.

The alkaline form of the zeolite with a hexagonal symmetry structure and an Si:Al ratio higher than 3 can be obtained in particular by using a process which consists in first of all producing a reaction mixture which has a pH higher than 10 and contains water, a source of tetravalent silicon, a source of trivalent aluminium, a source of hydroxide ions in the form of a strong base and a structuring agent ST consisting of at least one macrocyclic compound whose ring contains at least 18 atoms and includes heteroatoms chosen from oxygen, nitrogen, silicon and sulphur, so as to obtain an aluminosilicate gel which has the composition required to permit its crystallisation as the desired zeolite, in then maintaining the gel obtained, optionally after preliminary aging, at a temperature of not more than 150° C. and at a pressure at least equal to the autogenous pressure of the mixture consisting of the said gel for a period of time sufficient to produce the crystallisation of this gel as a precursor of the alkaline zeolite consisting of the said zeolite trapping the structuring agent ST in its cavities, and in subjecting the said precursor to a calcination to destroy the structuring agent and to produce the alkaline zeolite.

The quantity of structuring agent ST present in the reaction mixture intended to form the gel is advantageously such that the molar ratio $ST:Al^{III}$ ranges from 0.1 to 4, the said ratio preferably ranging from 0.1 to 1 and very particularly from 0.2 to 0.5.

In particular, the ingredients forming the reaction mixture giving rise to the aluminosilicate gel are employed so that the said gel has the following composition in terms of molar ratios:

|  | Advantageous ranges | Preferred ranges |
|---|---|---|
| $Si^{IV}:Al^{III}$ | 2 to 20 | 4 to 10 |
| $OH^-:Al^{III}$ | 0.5 to 8 | 1 to 6 |
| $ST:Al^{III}$ | 0.1 to 4 | 0.1 to 1 |
| $H_2O:Al^{III}$ | 40 to 200 | 50 to 150 |

The structuring agents ST which can be employed to constitute the reaction mixture giving rise to the aluminosilicate gel may be especially crown ethers whose ring contains 18 to 24 atoms and includes solely oxygen atoms as heteroatoms, among which there may be mentioned the following compounds:

1,4,7,10,13,16-hexaoxacyclooctadecane (crown ether "18-crown-6"), 2,3,11,12-dibenzo-1,4,7,10,13,16-hexaoxacyclooctadecane (crown ether "dibenzo-18-crown-6")

2,3,11,12-dicyclohexano-1,4,7,10,13,16-hexaoxacyclooctadecane (crown ether "dicyclohexano-18-crown-6") , 2,3,14,15-dibenzo-1,4,7,10,13,16,19,22-octaoxacyclotetracosane (crown ether "dibenzo-24-crown-8"), 2,3,14,15-dicyclohexano-1,4,7,10,13,16,19,22-octaoxacyclotetracosane (crown ether "dicyclohexano-24-crown-8"), compounds which have a structure comparable to that of the above crown ethers but in which the oxygen atoms in the ring are partially or wholly replaced by substituents chosen from sulphur atoms and $>NH$, $>NR$ and

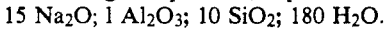

groups in which R is a $C_1$–$C_4$ hydrocarbyl radical, among which the following compounds may be mentioned:

1,4,7,10,13,16-hexaazacyclooctadecane trisulphate (hexacyclene trisulphate), 20-(1,1-dimethylsila)-1,4,7,10,13,16,19-heptaoxacycloeicosane (crown ether "dimethylsila-20-crown-7"), 1,4,7,10,13,16-hexathiacyclooctadecane, 1,7,10,16-tetraoxa-4,13-diazacyclooctadecane (Kryptofix 22).

Among the sources of tetravalent silicon $Si^{IV}$ which can be employed in the preparation of the reaction mixture intended to form the aluminosilicate gel there may be mentioned finely divided solid silicas in the form of hydrogels, aerogels or colloidal suspensions, water-soluble silicates such as alkali metal silicates like sodium silicate, and hydrolysable silicic esters such as tetraalkylorthosilicates of formula $Si(OR)_4$ in which R is a $C_1$–$C_4$ alkyl such as methyl or ethyl. The source of silicon is used in the form of a true aqueous solution, in the case of water-soluble silicates, or of an aqueous suspension which may be colloidal, in the case of finely divided silicas.

Materials suitable as sources of trivalent aluminium $Al^{III}$ are aluminium salts such as aluminium sulphate, nitrate, chloride, fluoride, acetate, oxides and hydroxyoxides, aluminates and especially alkali metal aluminates such as sodium aluminate, and aluminium esters such as aluminium trialkoxides of formula $Al(OR)_3$ in which R denotes a $C_1$–$C_4$ alkyl radical such as methyl, ethyl or propyl.

The source of hydroxide ions is chosen especially from alkali metal hydroxides, the hydroxides of the alkaline-earth metals Ca, Sr and Ba, and strong organic bases, especially quaternary ammonium hydroxides, preference being given to the inorganic bases and especially to sodium hydroxide NAOH.

The reaction mixture intended to form the aluminosilicate gel may also contain cations $M^{n+}$ and $M_1^{1+}$ as defined above and, in the case of the $M_1^{1+}$ cations, other than those of the strong base. The said cations may be introduced into the said reaction mixture in the form of salts such as sulphates, nitrates, chlorides or acetates or else in the form of oxides and in an overall quantity such that the molar ratio $(^{n+}+M_1^{1+}):Al^{III}$ is not more than 0.4 and preferably not more than 0.3.

Mixing of the ingredients constituting the reaction mixture intended to f orm the aluminosilicate gel may be carried out in any order whatever. The said mixing is advantageously carried out by first of all preparing, at room temperature, a basic aqueous solution containing a strong base and the structuring agent, and then incorporating into this solution an aqueous solution of the source of trivalent aluminium and an aqueous solution or a suspension, colloidal or otherwise, of the source of tetravalent silicon.

The pH of the reaction mixture is higher than 10 and preferably close to 13.

Before carrying on with the crystallisation of the gel, crystallisation nuclei may be added to the reaction mixture intended to form the said gel, in a quantity advantageously ranging from 0.1 to 10% by weight of the reaction mixture. These nuclei may be produced either by milling a zeolite of the same kind as the crystalline phase to be produced or else by synthesis from an appropriate nucleating solution. Such a solution has, for example, the following composition, expressed as oxides:

15 $Na_2O$; 1 $Al_2O_3$; 10 $SiO_2$; 180 $H_2O$.

In the absence of addition of nuclei it is advantageous to subject the aluminosilicate gel formed from the reaction mixture to aging in a closed vessel at a temperature below the crystallisation temperature for a period which can range from approximately 6 hours to approximately 6 days. The said aging may be carried out in static conditions or with stirring.

The crystallisation of the aluminosilicate gel, with or without nuclei, takes place by heating the reaction mixture to a temperature of not more than 150° C. and preferably ranging from 90° C. to 120° C. and at a pressure corresponding at least to the autogenous pressure of the reaction mixture forming the gel. The heating period needed for the crystallisation is generally between 2 hours and a fortnight.

The crystals obtained, which consist of the alkaline zeolite trapping the structuring agent in its pores and cavities, are separated from the crystallisation medium by filtration and are then washed with distilled or deionised water until aqueous washings whose pH is lower than 9 are obtained. The washed crystals are then dried in an oven at a temperature of between 50° C. and 100° C. and preferably in the region of 70° C.

The alkaline zeolite is obtained from the dried crystals by subjecting the said crystals to a calcination at a temperature above 300° C. and preferably between 400° C. and 700° C. for a period of time sufficient to remove the structuring agent which they contain.

The protonated (acidic) form of the zeolite is prepared from the alkaline form obtained as described above by first of all placing the calcined alkaline zeolite in contact with an aqueous solution of an ammonium salt, the operation being performed at temperatures ranging, for example, from 50° C. to 100° C. to produce an exchange of the alkali or alkaline-earth metal cations of the alkaline zeolite with $NH_4^+$ cations, the operation being repeated a number of times if need be, and then subjecting the zeolite containing $NH_4^+$ cations to the action of appropriate temperatures to produce a thermal degradation of the $NH_4^+$ cations and to obtain the acidic form of the zeolite, that is to say the form in which all the cations $M^{n+}$ in the formula given above are $H^+$ cations.

The $M^{n+}$ cations other than $H^+$ may also be incorporated by placing the zeolite in its alkaline or acidic form in contact with solutions of metal compounds supplying the said cations $M^{n+}$. The form of the zeolite in which part or all of the cations $M^{n+}$ in the formula given above consist of the cations originating from the said metal compounds is thus obtained.

The process of synthesis described above produces zeolites whose lattice Si:Al ratio is equal to or higher than 3. If need be the said Si:Al ratio can be increased further by subjecting the zeolite, in its alkaline or acidic or exchanged form, to one of the known dealumination treatments for this purpose and, for example, to one of the treatments with steam, ethylenediaminetetraacetic acid, $SiCl_4$ or $(NH_4)_2SiF_6$, as mentioned above.

As indicated earlier, the zeolites employed in the catalyst according to the invention are zeolites which are related to faujasite and which have a structure of hexagonal symmetry and a network Si:Al ratio ranging from 3 to 30 and preferably from 3 to 20. These zeolites have parameters a, b and c of the hexagonal lattice such that a=b, 1. 72 nm≦a≦1.75 nm and 2.80 nm≦c≦2.86 nm, and, after calcination at 600° C. for 4 hours, exhibit an X-ray diffraction pattern comparable to that of Table I below.

The Si:Al ratio of the zeolite can be determined by chemical analysis or else by radiocrystallography (D.W. Breck: "Zeolite Molecular Sieves", publ. John Wiley and Sons, New York, 1974, page 94) or else by silicon-29 NMR (J. Klinowski: "Progress in NMR Spectroscopy", 1984, vol. 16, pages 237 to 309).

The X-ray diffraction pattern is obtained by means of a diffractometer by employing the conventional powder method with copper $K_\alpha$ radiation. An internal standard makes it possible to determine accurately the values of the angles $2\theta$ associated with the diffraction peaks. The various interlattice distances $d_{hkl}$, characteristic of the sample, are calculated from the Bragg relationship. The relative intensity I:Io assigned to each $d_{hkl}$ value is estimated from the height of the corresponding diffraction peak. A scale of symbols is employed to characterise this relative intensity as follows: VS=very strong, S=strong, mS=moderately strong, m=medium, mw=moderately weak, w=weak and vw=very weak.

The mean values of the interlattice distances have been given in the $d_{hkl}$ column of Table I. The error of measurement $\Delta(d_{hkl})$ consisting of ±0.2 and =0.008 must be assigned to each of these values. The variations which can be observed in relation to these mean values are essentially linked with the nature of the compensating cations and the Si:Al ratio of the zeolite. The same comments apply to the relative intensities I/Io.

TABLE I

| $2\theta$ (°) | $d_{hkl}(10^{-1}$ nm) | (h k l) | I/Io |
|---|---|---|---|
| 5.88 | 15.03 ± 0.2 | (1 0 0) | VS |
| 6.23 | 14.2 | (0 0 2) | VS |
| 6.66 | 13.3 | (1 0 1) | S |
| 8.40 | 10.52 | (1 0 2) | w |
| 10.19 | 8.68 ± 0.08 | (1 1 0) | S |
| 11.06 | 7.99 | (1 0 3) | mS |
| 11.78 | 7.51 | (2 0 0) | mS |
| 11.95 | 7.40 | (1 1 2) | mS |
| 13.49 | 6.56 | (2 0 2) | vw |
| 15.06 | 5.88 ± 0.05 | (2 0 3) | w |
| 15.58 | 5.68 | (0 0 5) | S |
| 15.89 | 5.57 | (2 1 1) | w |
| 16.73 | 5.29 | (1 0 5) | w |
| 17.18 | 5.16 | (2 0 4) | S |
| 18.22 | 4.87 | (2 1 3) | w |
| 18.79 | 4.72 | (1 1 5) | w |
| 19.67 | 4.51 | (1 0 6) | w |
| 20.45 | 4.34 | (2 2 0) | mS |
| 22.22 | 4.00 | (3 1 2) | w |
| 22.75 | 3.91 | (1 0 7) | w |
| 23.30 | 3.82 | (3 1 3) | w |
| 23.66 | 3.76 | (3 0 5) | S |
| 24.75 | 3.59 | (3 1 4) | w |
| 25.83 | 3.45 | (2 2 5) | w |
| 26.52 | 3.36 | (2 1 5) | w |
| 27.16 | 3.28 | (4 1 0) | w |
| 28.77 | 3.103 ± 0.008 | (3 2 4) | w |
| 30.38 | 2.942 | (4 0 6) | vw |
| 30.89 | 2.894 | (3 3 0) | w |
| 31.20 | 2.866 | (5 0 3) | w |
| 31.56 | 2.834 | (3 3 2) | vw |

The inorganic binder which is associated with the zeolite to form the catalyst according to the invention may be inert, that is to say without any catalytic effect in the reaction for which the catalyst is employed, or else may be active, that is to say may exhibit some catalytic activity in the case of the reaction in question. The inorganic binder may consist especially of one or more refractory oxides such as, for example, alumina, silica, silica/alumina, clay or magnesia. The inorganic binder may also consist of a catalyst exhibiting an activity in the case of a reaction and in the case of which the addition of a zeolite according to the invention substantially improves the said activity or contributes a catalytic activity in another reaction.

The catalyst according to the invention may be prepared from the inorganic binder and the zeolite by making use of the various techniques proposed for this purpose. It is possible, in particular, to use an extrusion technique consisting in preparing a paste from appropriate quantities of the inorganic binder and of the zeolite and a small quantity of water and then subjecting the paste thus formed to an extrusion through a die to form granules. The catalyst may also be prepared in the form of microspheres by spray-drying an aqueous suspension of the inorganic binder and of the zeolite. It is also possible to form the catalyst from the inorganic binder and zeolite by employing a pelleting or coating technique.

The forming of the catalyst may also be carried out by starting with the inorganic binder and the alkaline form of the zeolite, after which the product resulting from this forming is subjected to the operations described above to obtain the form of the zeolite containing $H^+$ cations and/or metal cations $M^{n+}$.

When the catalyst according to the invention contains a metal or a metal compound in addition to the compensating metal cations of the zeolite, the said metal or metal compound is incorporated into the catalyst by any known method, for example by addition to the mixture of the inorganic binder and of the zeolite before the forming of the said mixture, by impregnation of the inorganic binder and/or of the zeolite before the latter are mixed or else by impregnation of the product resulting from the forming of the mixture of the inorganic binder and of the zeolite.

The catalyst according to the invention can be employed for promoting acidic catalysis reactions carried out on hydrocarbon feedstocks.

In particular, the said catalyst is suitable for the catalytic cracking of hydrocarbon feedstocks, especially catalytic cracking of vacuum distillates or of residues into petrol, the operation being carried out in particular in a fluidised bed ("Fluid Catalytic Cracking" abbreviated to FCC) or in a moving bed at temperatures ranging, for example, from 450° C. to 650° C.

The catalyst according to the invention is further suitable for promoting the hydrocracking of hydrocarbon feedstocks, in particular the hydrocracking of vacuum distillates to diesel fuel, the operation being carried out at temperatures above 250° C., especially between 350° C. and 500° C. at a pressure above 15 bars, advantageously above 30 bars and with an hourly space velocity of between 0.2 and 10.

The abovementioned catalyst is also suitable for promoting the alkylation of aromatic hydrocarbons, especially benzene, using olefins, and the isomerisation of alkylaromatic hydrocarbons such as xylenes.

The zeolite present in the catalyst has a specific surface, determined by nitrogen adsorption according to the B.E.T. method simplified to a point (NF standard X 11-622), of between 100 m²/g and 1,000 m²/g and preferably between 300 m²/g and 900 m²/g.

The following examples are given to illustrate the invention, no limitation being implied.

EXAMPLE 1

Synthesis of an acidic zeolite related to faulasite and exhibiting a structure of hexagonal etry and an Si:Al ratio higher than 3

An aluminosilicate gel was prepared first of all by operating as follows in a vessel of appropriate capacity, the contents of the said vessel being kept stirred throughout the operation.

9 parts of water were introduced into the vessel, followed by 0.44 parts of sodium hydroxide NAOH and, after the sodium hydroxide had dissolved, 1.45 parts of crown ether 18-crown-6. After the crown ether had dissolved completely, 1 part of a sodium aluminate containing 56% of $Al_2O_3$ and 37% of $Na_2O$ was then added to the contents of the vessel and the reaction mixture was heated slightly to dissolve the aluminate completely. After returning to room temperature, 8.2 parts of a colloidal suspension of silica containing 40% of $SiO_2$ and 60% of water were then introduced into the vessel.

An aluminosilicate gel was thus obtained, whose molar composition, normalised to one mole of $Al_2O_3$, was as follows:

10 $SiO_2$; 1 $Al_2O_3$; 2.1 $Na_2O$; 1 crown ether; 140 $H_2O$

The gel obtained was subjected to aging at room temperature for 24 hours in a closed vessel.

The aged gel was then placed in an autoclave and maintained in the latter at 1100° C. for 336 hours to form a crystallised product. The crystals formed were separated from the reaction medium by filtration and then washed with distilled water to low basicity (pH below 9) of the aqueous washes and were finally dried in an oven at approximately 60° C.

The dried crystals were then calcined to remove the crown ether employed as structuring agent, the said calcination being carried out under a light flow of air equal to 1.5 l h$^{-1}$ using the following thermal profile

| temperature gradient | | duration (min) |
| --- | --- | --- |
| 20° C. | 100° C. | 30 |
| 100° C. | 100° C. | 60 |
| 100° C. | 200° C. | 30 |
| 200° C. | 200° C. | 60 |
| 200° C. | 450° C. | 60 |
| 450° C. | 450° C. | 180 |
| 450° C. | 25° C. | (oven inertia) |

The solid obtained after calcination, which consists of the alkaline form of the zeolite, exhibited an X-ray diffraction pattern comparable with that of Table I, characteristic of the calcined zeolites exhibiting a structure of hexagonal symmetry and related to faujasite. The formula found for this zeolite, normalised to one unit cell of the hexagonal structure, is written in the anhydrous state

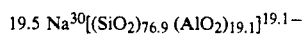

A very slight excess of positive charge is observed, relative to neutrality.

The calcined solid, consisting of the calcined sodium form of the zeolite, was placed in contact with a two-molar solution of $NH_4NO_3$ to carry out an exchange of the $Na^+$ cations of the zeolite with $NH_4^+$ cations, the operating conditions of the exchange operation being as follows:
volume of liquid per g of solid: 25 ml
temperature of the exchange: 80° C.
duration of the exchange: 1.5 hours The exchange operation was repeated five times.

The acidic form of the zeolite was then obtained by thermal degradation of the ammonium cations present in the zeolite subjected to the exchange, the said thermal degradation being carried out under a light flow of air of 1.5 l/hour using the following thermal profile:

| temperature gradient | | duration (min) |
| --- | --- | --- |
| 20° C. | 200° C. | 120 |
| 200° C. | 200° C. | 60 |
| 200° C. | 550° C. | 240 |
| 550° C. | 550° C. | 180 |
| 550° C. | 25° C. | (oven inertia) |

The acidic zeolite resulting from the above thermal treatment was then placed in the humidifier at a relative humidity of 80% so as to stabilise its degree of hydration.

The acidic zeolite obtained had a structure of hexagonal symmetry and an Si:Al ratio equal to approximately 4 and exhibited an X-ray diffraction pattern comparable with that of Table I, the parameters a, b and c of the hexagonal lattice being such that a=b=1.74 nm and c=2.83 nm. The crystalline fraction content of this acidic zeolite, determined by X-ray diffraction, was equal to 100%.

The chemical weight composition as oxides of the dehydrated acidic zeolite as shown above is as follows:

| Na$_2$O | SiO$_2$ | Al$_2$O$_3$ | H$_2$O |
|---|---|---|---|
| 0.31% | 60.10% | 12.67% | 26.9% |

The formula found for this zeolite, normalised to one unit cell of the hexagonal structure, is written in the anhydrous state (t=0 in the general formula):

$$(0.8\ Na^+)\ (18.3\ H^+)\ [(SiO_2)_{76.9}\ (AlO_2)_{19.1}]^{19.1-}$$

EXAMPLE 9

Study the acid programmed thermodesorption of ammonia

The distribution of the acidic sites of the following three acidic zeolites was studied by using the technique of programmed thermodesorption of ammonia:

A) acidic zeolite according to the invention obtained as described in Example 1;

B) acidic zeolite of faujasite type (cubic symmetry) obtained by subjecting a zeolite Y in its ammonium form NH$_4$Y, which is marketed under the name ZF 110 by Zeocat, to a treatment of thermal degradation of the NH$_4^+$cations identical with that described in Example 1. After rehydration in a relative humidity of 80%, this acidic zeolite had the physicochemical characteristics given in Table II below.

TABLE II

| Chemical weight composition as oxides (%) | | | | Measured Si:Al ratio | Crystalline fraction* (%) |
|---|---|---|---|---|---|
| Na$_2$O | SiO$_2$ | Al$_2$O$_3$ | H$_2$O | | |
| 1.14 | 53.44 | 17.62 | 27.80 | 26 | 90 |

*The reference employed is the acidic zeolite of Example 1.

The formula found for zeolite ZF 110 in its acidic form, normalised to one unit cell of its cubic structure, is written in the anhydrous state $$(5.7\ Na^+)(47.9\ H^+)[(SiO_2)_{138.4}\ (AlO_2)_{53.6}]^{53.6-}$$

C) acidic zeolite of faujaste type (cubic symmetry) consisting of the acidic form of a commercial dealuminised zeolite y (zeolite ZF 510 from Zeocate) without alumina debris.

The phyusicochemical characteristics of the sample of this a idic zeolite after rehydration under a relative humidity of 80% are given in Table III.

TABLE III

| Chemical weight composition as oxides (%) | | | | Measured Si:Al ratio | Crystalline fraction* (%) |
|---|---|---|---|---|---|
| Na$_2$O | SiO$_2$ | Al$_2$O$_3$ | H$_2$O | | |
| 0.2 | 66.6 | 6.64 | 26.6 | 8.5 | 95 |

*The reference employed is the acidic zeolite of Example 1.

"The formula found for the acidic zeolite ZF 510, normalised to one unit cell of its cubic structure, is written in the anhydrous state $$(1.0\ Na^+)\ (19.2H^+)[(SiO_2)_{171.8}\ (AlO_2)_{20.2}]^{20.2-}$$

The successive operations carried out during each thermodesorption test were carried out under a light flow of gas, these operations being outlined in Table IV

TABLE IV

| Operation | Temperature (°C.) | Duration (min) | Gas Nature | Flow rate (l/h) |
|---|---|---|---|---|
| Activation of the zeolite in two stages | 200 / 550 | 30 / 60 | helium | 1.5 |
| NH$_3$ adsorption | 100 | 15 | NH$_3$ | 1.5 |
| Purge of the excess NH$_3$ | 140 | 30 | NH$_3$ | 4.0 |
| NH$_3$ desorption (a desorption plateau of 60 minutes is carried out at each temperature) | 200 | 60 | | |
| | 250 | 60 | | |
| | 300 | 60 | | |
| | 350 | 60 | helium | 1.5 |
| | 400 | 60 | | |
| | 450 | 60 | | |
| | 500 | 60 | | |
| | 550 | 60 | | |

From the volume of NH$_3$ released at each desorption plateau a determination was made of the corresponding quantity of H$^+$ cations and this quantity was normalised as milliequivalents per gram (meq. H$^+$/g) of the acidic zeolite subjected to the thermodesorption test.

The results obtained are collated in Table V.

TABLE V

| Temperature (°C.) | Quantity of H$^+$ in the acidic zeolite (meq. H$^+$/g) | | |
|---|---|---|---|
| | Acidic zeolite A | Acidic zeolite B | Acidic zeolite C |
| 150 | 0.034 | 0.040 | 0.029 |
| 200 | 0.487 | 0.297 | 0.226 |
| 250 | 0.422 | 0.257 | 0.215 |
| 300 | 0.371 | 0.229 | 0.213 |
| 350 | 0.398 | 0.197 | 0.214 |
| 400 | 0.344 | 0.142 | 0.124 |
| 450 | 0.152 | 0.086 | 0.044 |
| 500 | 0.054 | 0.052 | 0.026 |
| 550 | 0.049 | 0.043 | 0.029 |
| Total acidity | 2.311 | 1.343 | 1.120 |

In the light of the results presented in Table V it appears that the density of acidic sites and the number of high-acidity sites are higher in the acidic zeolite A (according to the invention) than in the control acidic zeolites B and C.

EXAMPLE 3

Catalytic activity of the acidic zeolite in n-heptane cracking

The catalytic activities of acidic zeolite A according to the invention and of each of the control acidic zeolites B and C of Example 2 were evaluated in catalytic cracking of n-heptane.

To do this, the operation was carried out in a quartz reactor of 18 mm internal diameter, equipped in its centre with a sintered glass plate on which were placed 500 mg of the acidic zeolite to be subjected to the test. After the zeolite placed on the glass plate had been activated by heating at 200° C. for 30 min and then at 550° C. for 60 min under a stream of nitrogen flowing at a rate of 1.5 1/hour, a mixture of nitrogen and n-heptane was passed over the activated zeolite. The operating conditions were as follows:

| | |
|---|---|
| pressure: | atmospheric |
| ratio of the partial pressures $p_{N_2}:P_{n-heptane}$: | 6.6 |
| reaction temperature: | 350° C. |
| (weight of reactant/weight of zeolite) per hour | 2.4 h$^{-1}$ |

The value of the catlystic acitivity, expressed in millimoles of cracked n-heptane per gram of zeolite per hour (mmol h$^{-1}$g$^{-1}$) is given in Table VI as a function of the reaction time of the zeolite in minutes (min).

TABLE VI

| | n-Heptane cracked (mmol h$^{-1}$g$^{-1}$) | | |
|---|---|---|---|
| Reaction time (min) | Acidic zeolite A | Acidic zeolite B | Acidic zeolite C |
| 8 | 22.90 | 3.61 | 13.88 |
| 18 | 16.69 | 2.69 | 8.31 |
| 28 | 13.07 | 2.25 | 5.67 |
| 38 | 11.00 | 1.88 | 4.72 |
| 48 | 8.83 | 1.55 | 3.90 |
| 68 | 6.53 | 1.29 | 2.47 |
| 125 | 3.10 | 0.64 | 1.17 |

The above results clearly show that the acidic zeolite A according to the invention exhibits a catalytic activity which is superior to those of the control acidic zeolites B and C.

EXAMPLE 4

Thermal stability of the acidic zeolite

Samples of acidic zeolite A (according to the invention) and of the control acidic zeolites B and C of Example 2 were calcined at 800° C. for 4 hours under a flow of dry air at the rate of 1.5 1/hour.

The calcined products obtained were rehydrated under a relative humidity of 80%, after which their degrees of crystallinity were determined by X-ray diffraction, the acidic zeolite A (acidic zeolite of Example 1) being taken as reference.

The degrees of crystallinity of zeolites A, B and C, which were calcined as shown above, were 90% (calcined A), 25% (calcined B) and 110% (calcined C) respectively.

EXAMPLE 5

Effect of thermal stability of the acidic zeolite on its catalyst characteristics The calcined acidic zeolites A and C of Example 4, which are comparable in crystallinity, were subjected to the programmed NH3 thermodesorption test as shown in Example 2 and also to the catalytic cracking of n-heptane test as shown in Example 3.

The results of these tests are presented in Tables VII and VIII respectively.

TABLE VII

| Programmed thermodesorption of NH$_3$ | | |
|---|---|---|
| | Acidity (meq. H$^+$/g) | |
| Temperature (°C.) | Calcined zeolite A of Example 4 | Calcined zeolite C of Example 4 |
| 150 | 0.097 | 0.032 |
| 200 | 0.287 | 0.180 |
| 250 | 0.219 | 0.130 |
| 300 | 0.157 | 0.099 |

TABLE VII-continued

| Programmed thermodesorption of NH$_3$ | | |
|---|---|---|
| | Acidity (meq. H$^+$/g) | |
| Temperature (°C.) | Calcined zeolite A of Example 4 | Calcined zeolite C of Example 4 |
| 350 | 0.137 | 0.076 |
| 400 | 0.068 | 0.045 |
| 450 | 0.024 | 0.019 |
| 500 | 0.021 | 0.014 |
| 550 | 0.021 | 0.016 |
| Total acidity | 1.031 | 0.611 |

TABLE VIII

| | Cracking of n-heptane n-Heptane cracked (mmol h$^{-1}$g$^{-1}$) | |
|---|---|---|
| Reaction time (min) | Calcined zeolite A of Example 4 | Calcined zeolite C of Example 4 |
| 8 | 10.11 | 3.8 |
| 18 | 6.31 | 2.13 |
| 28 | 4.65 | 1.62 |
| 38 | 3.28 | 1.22 |
| 48 | 2.76 | 0.99 |
| 68 | 1.97 | 0.51 |
| 125 | 0.52 | 0.19 |

Again, after calcination at 800° C. under air, the acidic zeolite according to the invention (zeolite A) has catalyst characteristics which are superior to those of the control zeolite C calcined under the same conditions.

EXAMPLE 6

Hydrothermal stability of acidic zeolite

The specific surface of samples of acidic zeolites A, B and C of Example 2 and of an US acidic zeolite Y (ultrastabilized acidic zeolite Y) supplied by Katalistiks (acidic zeolite D) was determined before and after the said samples were subjected to the action of 100% steam at 750° C. for 2 hours.

The determination of the specific surfaces was performed by nitrogen adsorption according to the B.E.T. method simplified to one point.

The results obtained are collated in Table IX.

TABLE IX

| | Specific surface (m$^2$/g) | | |
|---|---|---|---|
| Acidic zeolite employed | Before steam treatment | After steam treatment | Surface retention (%) |
| A | 632 | 460 | 73 |
| B | 585 | 9 | 1.5 |
| C | 615 | 542 | 88 |
| D | 562 | 432 | 77 |

The lattice Si:Al ratio of acidic zeolite D is approximately 4.

EXAMPLE 7

Laboratory test to evaluate the catalyst activity on actual feedstock-("microactivity test")

The efficiency of two catalysts A (according to the invention) and D (comparative) as cracking catalysts in fluidized bed (FCC) was determined by employing the laboratory method ("microactivity test") defined in ASTM standard D 3907-87. The hydrocarbon feedstock treated was an actual feedstock taken from a refinery, whose characteristics are summarized below:

$d_4^{15}$ = 0.922 aniline point 82.1° C.

viscosity at 100° C. = 6.08 × 10$^{-6}$ M$^2$/s
sulphur content = 2.68% by weight
content of nitrogen compounds = 800 ppm (expressed as nitrogen)
Conradson carbon = 0.44%
distillation according to ASTM D 1160

| | |
|---|---|
| 5% | 324° C. |
| 10% | 362° C. |
| 50% | 431° C. |
| 90% | 502° C. |
| 95% | 519° C. |

The catalysts A and D employed were the following:

Catalyst A (according to the invention): obtained from a mixture containing, by weight, 95% of a catalyst E and 5% of the acidic zeolite A of Example 3 (acidic zeolite of Example 1). Catalyst E consisted of an industrial catalytic cracking catalyst from Crosfield (catalyst SLS 100) subjected to a steam treatment at 750° C. for 17 hours under 100% steam.

Catalyst D (comparative): obtained from a mixture containing, by weight, 95% of the abovementioned catalyst E and 5% of acidic zeolite D.

The operating conditions employed in the test were as shown below:

| | |
|---|---|
| quantity of catalyst: | 3 g |
| reactor temperature: | 530° C. |
| catalyst:feedstock weight ratio: | 6 |
| (weight of feedstock/weight of catalyst)/h: | (30 g/g)/hour |

The results obtained are summarised in Table X.

These results demonstrate that catalyst A has an activity equivalent to that of catalyst D. Furthermore, catalyst A exhibits a better selectivity for coke and for petrol, the LPGs obtained being richer in olefins, allowing a higher octane value to be predicted int h case of the petrols obtained.

TABLE X

| | Catalyst A | Catalyst D |
|---|---|---|
| Yields (weight %) | 8.04 | 8.55 |
| Coke | 0.08 | 0.09 |
| H$_2$ | 1.23 | 1.32 |
| C$_1$ | 2.22 | 2.42 |
| Gas (H$_2$ + C$_1$ + C$_2$) | 3.53 | 3.83 |
| C$_3$ | 3.57 | 4.43 |
| C$_3$= | 4.63 | 4.16 |
| iso C$_4$ | 6.88 | 7.18 |
| n-C$_4$ | 2.29 | 2.55 |
| C$_4$= | 4.84 | 4.38 |
| LPG (ΣC$_3$ + ΣC$_4$) | 22.21 | 22.70 |
| Total gas | 25.74 | 26.53 |
| Total petrol (final point 220° C.) | 46.19 | 45.28 |
| Conversion (weight %) (Petrol + gas + coke) | 79.97 | 80.36 |
| Diesel fuel (220° C.–350° C.) | 13.87 | 13.45 |
| Residues (>350° C.) | 6.16 | 6.19 |
| C$_3$=:ΣC$_3$ ratio | 0.56 | 0.48 |
| C$_4$=:ΣC$_4$ ratio | 0.35 | 0.31 |

We claim:

1. A catalyst comprising by weight, y% of an inorganic binder and z% of a zeolite with a structure of hexagonal symmetry related to faujasite, y and z being numbers such that $1 < y < 99$ and $1 \leq z \leq 99$ with $y + z = 100$, the said zeolite exhibiting an Si:Al ratio ranging from 3 to 30, and parameters a, b and c of its hexagonal lattice such that $1.72 \text{ nm} \leq a = b \leq 1.75$ nm and $2.80 \text{ nm} \leq c \leq 2.86$ nm and corresponding to a formula which, normalized to a unit cell of the hexagonal structure, is written

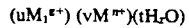

$$(uM_1^{x+})(vM^{n+})(tH_2O)$$

with, in this formula, M$^{n+}$ denoting cations of at least one element of valency n chosen from H, B, Al, Ga, In, the rare earth metals and the transition metals, M$_1^{g+}$ denoting cations of at least one metal of valency q chosen from the alkali metals and the alkaline-earth metals, and u, v, x and t are numbers such that $t \geq 0$ depending on the degree of hydration of the zeolite, $t = 0$ in the case of a completely anhydrous zeolite, and that $qu + vn \geq x$ with $0.5x \leq vn \leq x$ and $3 < x < 24$.

2. The catalyst according to claim 1, wherein the proportions y% of the inorganic binder and z% of the zeolite are such that $4 \leq y \leq 96$ and $4 \leq z \leq 96$ with $y + 100$.

3. The catalyst according to claim 1, wherein the zeolite, exhibits an Si:Al ratio ranging from 3 to 20.

4. The catalyst according to claim 1, characterised in that the number v of cations M$^{n+}$ in the formula of the zeolite is such that $0.8x \leq vn \leq x$.

5. The catalyst according to claim 1, characterised in that M$_1^{g+}$ in the formula of the zeolite denotes cations of at least one element chosen from Na, K, Li, Cs, Ca, Sr and Ba, while M$^{n+}$ denotes cations of at least one element taken from H, B, Al, Ga, In, transition metals and rare earths.

6. The catalyst according to claim 1, characterised in that M$^{n+}$ in the formula of the zeolite denotes solely H$^+$.

7. The catalyst according to claim 1, characterised in that the zeolite present in the catalyst has a specific surface, determined by nitrogen adsorption according to the B.E.T. method simplified to a point (NF standard X 11-622), of between 100 m$^2$/g and 1,000 m$^2$/g.

8. The catalyst according to claim 1, characterised in that, in addition to the binder and to the zeolite, it contains up to 15% by weight of the binder and zeolite combined, of at least one catalytically active metal present in the elemental state or in the form of a metal compound and chosen from noble metals and nonnoble transition metals.

9. The catalyst according to claim 1, characterised in that the inorganic binder consists of at least one refractory oxides chosen from alumina, silica, clay, silica/alumina and magnesia.

10. The catalyst according to claim 1, wherein the zeolite present in the catalyst has a specific surface, determined by nitrogen adsorption according to the B.E.T. method simplified to a point (NF standard S 11-622), of between 300 m$^2$/g and 900 m$^2$/g.

11. The catalyst according to claim 1, wherein in addition to the binder and to the zeolite, it contains up to 10% by weight of the binder and zeolite combined, of at least one catalytically active metal present in the elemental state or in the form of a metal compound and selected from the group consisting of platinum, palladium, rhodium, iridium, nickel, cobalt, tungsten, molybdenum and gallium.

12. The catalyst according to claim 1, wherein after calcination at 600° c. for 4 hours, the zeolite exhibits an X-ray diffraction pattern comparable with tat given in the following table:

| 2θ (°) | $d_{hkl}$ ($10^{-1}$ nm) | (h k l) | I/Io |
|---|---|---|---|
| 5.88 | 15.03 ± 0.2 | (1 0 0) | VS |
| 6.23 | 14.2 | (0 0 2) | VS |
| 6.66 | 13.3 | (1 0 1) | S |
| 8.40 | 10.52 | (1 0 2) | w |
| 10.19 | 8.68 ± 0.08 | (1 1 0) | S |
| 11.06 | 7.99 | (1 0 3) | mS |
| 11.78 | 7.51 | (2 0 0) | mS |
| 11.95 | 7.40 | (1 1 2) | mS |
| 13.49 | 6.56 | (2 0 2) | vw |
| 15.06 | 5.88 ± 0.05 | (2 0 3) | w |
| 15.58 | 5.68 | (0 0 5) | S |
| 15.89 | 5.57 | (2 1 1) | w |
| 16.73 | 5.29 | (1 0 5) | w |
| 17.18 | 5.16 | (2 0 4) | S |
| 18.22 | 4.87 | (2 1 3) | w |

-continued

| 2θ (°) | $d_{hkl}$ ($10^{-1}$ nm) | (h k l) | I/Io |
|---|---|---|---|
| 18.79 | 4.72 | (1 1 5) | w |
| 19.67 | 4.51 | (1 0 6) | w |
| 20.45 | 4.34 | (2 2 0) | mS |
| 22.22 | 4.00 | (3 1 2) | w |
| 22.75 | 3.91 | (1 0 7) | w |
| 23.30 | 3.82 | (3 1 3) | w |
| 23.66 | 3.76 | (3 0 5) | S |
| 24.75 | 3.59 | (3 1 4) | w |
| 25.83 | 3.45 | (2 2 5) | w |
| 26.52 | 3.36 | (2 1 5) | w |
| 27.16 | 3.28 | (4 1 0) | w |
| 28.77 | 3.103 ± 0.008 | (3 2 4) | w |
| 30.38 | 2.942 | (4 0 6) | vw |
| 30.89 | 2.894 | (3 3 0) | w |
| 31.20 | 2.866 | (5 0 3) | w |
| 31.56 | 2.834 | (3 3 2) | vw |

* * * * *

UNITED STATES PATENT AND TRADEMARK OFFICE
CERTIFICATE OF CORRECTION

PATENT NO. : 5,273,945
DATED : December 28, 1993
INVENTOR(S) : des Courieres et al.

It is certified that error appears in the above-indentified patent and that said Letters Patent is hereby corrected as shown below:

Column 1, lines 33 and 40: "U.S. application" should read --U.S. patent--.

Column 2, line 5: in the formula "$M_1^{I+}$" should read --$M_1^{q+}$-- and "$(AlO_2)$" should read --$(AlO_2)_x$--.

lines 8 and 32: "$M_1^{I+}$" should read --$M_1^{q+}$--.

Column 4, line 17: "NAOH" should read --NaOH--.

lines 19-20: "$M_1^{I+}$" first and second occurences should read --$M_1^{q+}$--.

line 25: the ratio should read --$(M^{n+} + M_1^{q+}):Al^{III}$--.

Column 6, line 5: "$=0.008$" should read --$\pm 0.008$--.

Column 7, line 50: "etry" should read --symmetry--.
line 58: "NAOH" should read --NaOH--.

Column 8, line 8: the temperature should read --110°C--.

line 37: in the formula "$Na^{30}$" should read --$Na^+$--.

UNITED STATES PATENT AND TRADEMARK OFFICE
CERTIFICATE OF CORRECTION

PATENT NO. : 5,273,945
DATED : December 28, 1993
INVENTOR(S) : des Courieres et al.

It is certified that error appears in the above-identified patent and that said Letters Patent is hereby corrected as shown below:

Column 9, line 24: "EXAMPLE 9" should read --EXAMPLE 2--.
line 25: add --of-- after "study".
line 56: "zeolite y" and "Zeocate" should respectively read --zeolite Y-- and --Zeocat--.
line 58: "phyusicochemical" should read --physicochemical--.
line 59: "a idic" should read --acidic--.

Column 11, line 13: "catlystic acitivity" should read --catalytic activity--.

Column 13, line 1: "M²/s" should be --m²/s--.

line 39: "int h" should read --in the--.

Column 14, line 5: the formula should read as follows:

$$--(uM_1^{q+})\ (vM^{n+})\ [(SiO_2)_{96-x}(AlO_2)_x]^{x-}(tH_2O)--.$$

lines 10 and 27: "$M_1^{g+}$" should read --$M_1^{q+}$--.

line 66: "600°c" should read --600°C--.

line 67: "tat" should read --that--.

UNITED STATES PATENT AND TRADEMARK OFFICE
CERTIFICATE OF CORRECTION

PATENT NO. : 5,273,945

DATED : December 28, 1993

INVENTOR(S) : des Courieres et al

It is certified that error appears in the above-indentified patent and that said Letters Patent is hereby corrected as shown below:

Column 14, line 67: "tat" should read --that--.

Signed and Sealed this

Twentieth Day of September, 1994

Attest:

BRUCE LEHMAN

*Attesting Officer*  *Commissioner of Patents and Trademarks*